(12) United States Patent
Marino

(10) Patent No.: US 7,690,844 B2
(45) Date of Patent: Apr. 6, 2010

(54) METHOD AND SYSTEM FOR GUIDANCE SYSTEM POSITIONER

(75) Inventor: James F. Marino, La Jolla, CA (US)

(73) Assignee: Trinity Orthopedics, San Diego, CA (US)

( * ) Notice: Subject to any disclaimer, the term of this patent is extended or adjusted under 35 U.S.C. 154(b) by 421 days.

(21) Appl. No.: 11/562,946

(22) Filed: Nov. 22, 2006

(65) Prior Publication Data

US 2007/0127626 A1     Jun. 7, 2007

(51) Int. Cl.
*H01J 31/49* (2006.01)
*H05G 1/02* (2006.01)

(52) U.S. Cl. ...................................... 378/189; 378/193
(58) Field of Classification Search ..................... 378/4, 378/19, 39, 41, 42, 198–197, 208
See application file for complete search history.

(56) References Cited

U.S. PATENT DOCUMENTS

| | | | |
|---|---|---|---|
| 2,232,014 A | 2/1941 | Simon | |
| 2,818,510 A | 12/1957 | Verse | |
| 3,593,013 A | 7/1971 | Mertes | |
| 4,341,279 A | 7/1982 | Waerve | |
| 4,481,656 A | 11/1984 | Janssen et al. | |
| 4,697,661 A | 10/1987 | Pajerski et al. | |
| 5,219,349 A | 6/1993 | Krag et al. | |
| 5,386,453 A | 1/1995 | Harrawood et al. | |
| 5,734,694 A | 3/1998 | Khutoryansky et al. | |
| 6,095,685 A | 8/2000 | Tamura | |
| 6,131,690 A | 10/2000 | Galando et al. | |
| 6,237,707 B1 | 5/2001 | Lyke et al. | |
| 6,374,937 B1 | 4/2002 | Galando et al. | |
| 6,461,039 B1 | 10/2002 | Klotz et al. | |
| 6,466,641 B1 | 10/2002 | Virta et al. | |
| 6,491,429 B1 | 12/2002 | Suhm | |
| 6,814,490 B1 | 11/2004 | Suhm et al. | |
| 6,830,375 B2 | 12/2004 | Deshpande | |
| 6,882,700 B2 | 4/2005 | Wang et al. | |
| 2003/0053599 A1 | 3/2003 | Meyer et al. | |
| 2003/0091156 A1 | 5/2003 | Crain et al. | |
| 2003/0099328 A1* | 5/2003 | Jensen et al. | 378/198 |
| 2004/0234039 A1 | 11/2004 | Karaus et al. | |
| 2005/0094770 A1 | 5/2005 | Fadler et al. | |
| 2005/0171420 A1 | 8/2005 | Boese et al. | |
| 2006/0039537 A1* | 2/2006 | Strobel | 378/197 |

FOREIGN PATENT DOCUMENTS

WO     WO 07/062133     5/2007

* cited by examiner

*Primary Examiner*—Irakli Kiknadze
(74) *Attorney, Agent, or Firm*—Fred C. Hernandez; Mintz, Levin, Cohn, Ferris, Glovsky and Popeo P.C.

(57) ABSTRACT

Apparatus and methods for incrementally positioning at least one adjustable axis of a guidance system where the guidance system may be an image based guidance system.

22 Claims, 17 Drawing Sheets

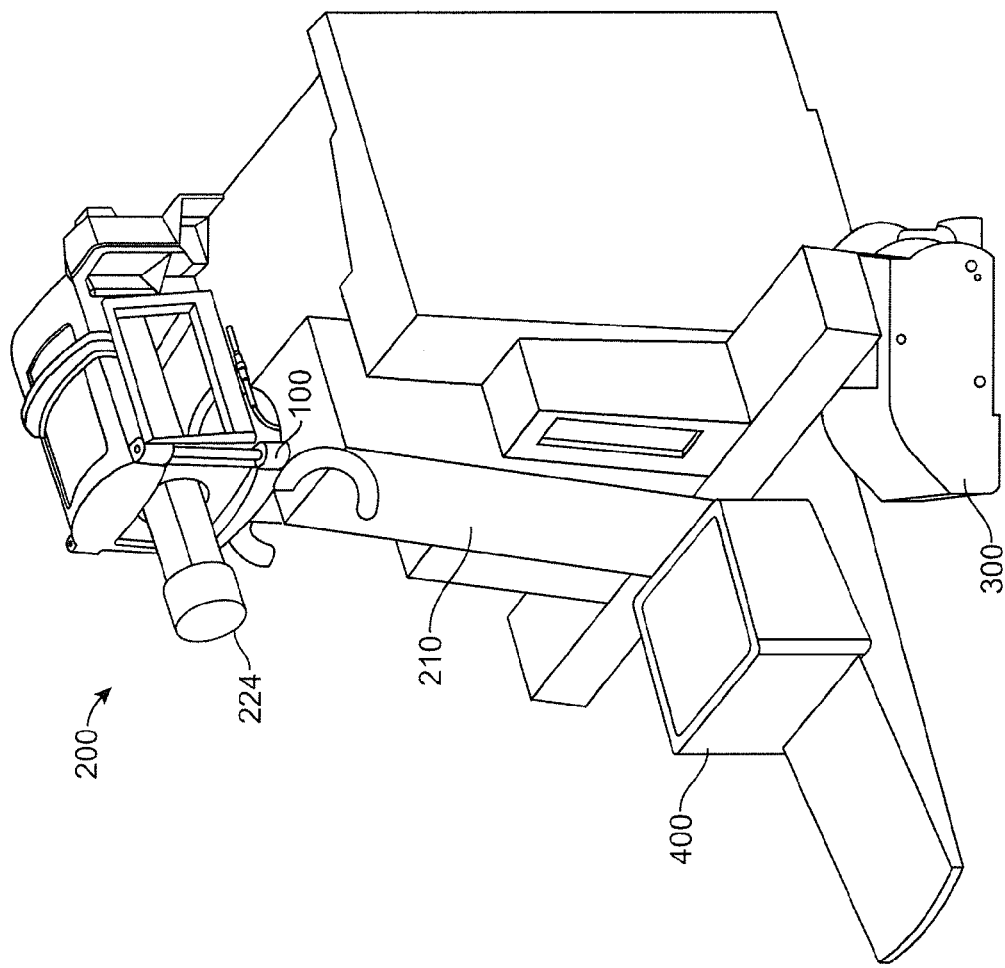
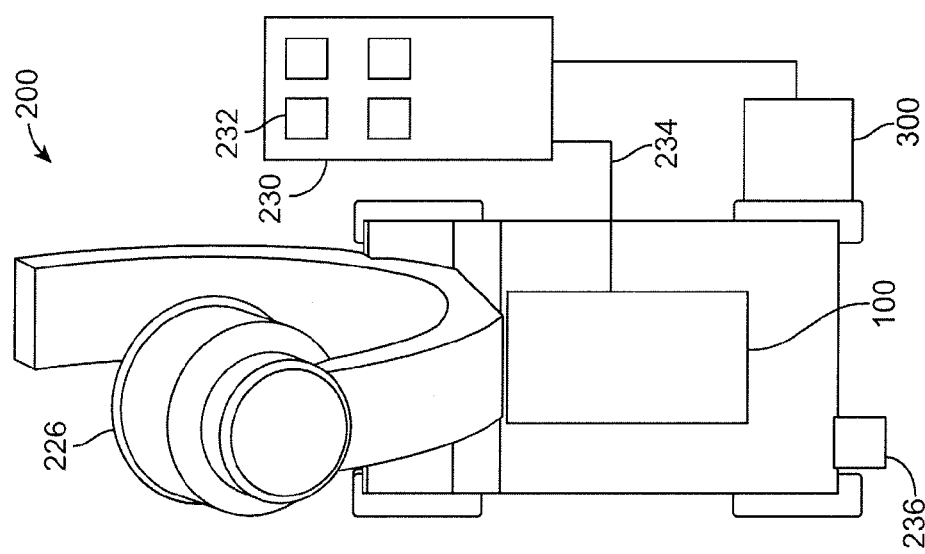
FIG. 1B
FIG. 1A

US 7,690,844 B2

METHOD AND SYSTEM FOR GUIDANCE SYSTEM POSITIONER

BACKGROUND

1. Field of the Invention

The invention relates generally to guidance systems and methods, and more particularly, to guidance positioning systems and methods.

2. Description of Related Art

It is desirable to enable a user to accurately or precisely position or re-position a guidance system including an image intensifier. The present invention provides such a system and method.

SUMMARY OF THE INVENTION

The present invention includes apparatus and methods for incrementally positioning at least one adjustable axis of a guidance system where the guidance system may be an image based guidance system.

BRIEF DESCRIPTION OF THE DRAWINGS

The features, objects, and advantages of the present invention will become more apparent from the detailed description set forth below when taken in conjunction with the drawings in which like reference characters identify correspondingly throughout and wherein:

FIG. 1A is a diagram of a guidance system including at least one electronic positioning device according to various embodiments;

FIG. 1B is a diagram of a segment of guidance system including at least one electronic positioning device according to various embodiments;

DETAILED DESCRIPTION

Throughout this description, embodiments and variations are described for the purpose of illustrating uses and implementations of the invention. The illustrative description should be understood as presenting examples of the invention, rather than as limiting the scope of the invention.

Figure 1C:
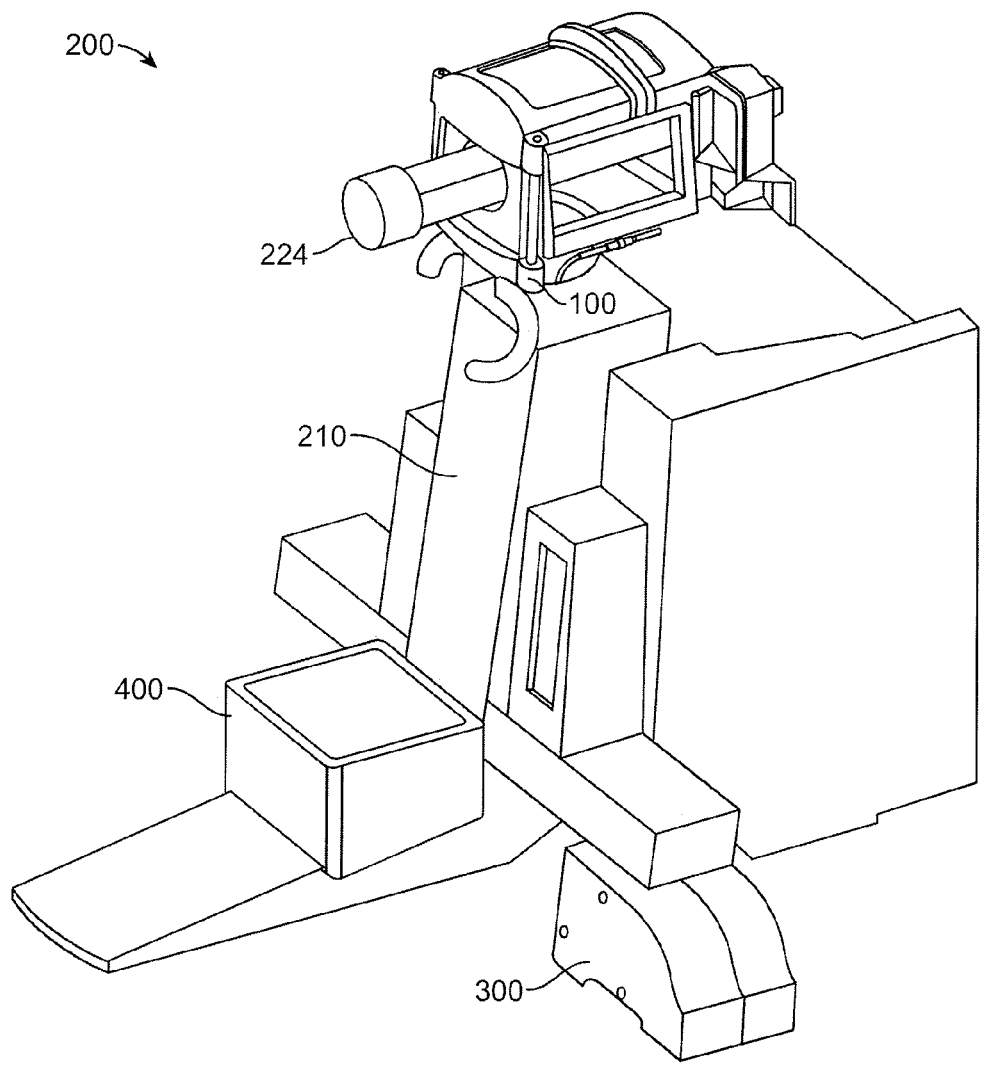
FIG. 1C is a diagram of a segment of guidance system including at least one electronic positioning device according to various embodiments.

FIG. 1A is a top view of block diagram of a guidance system 200 including at least one electronic positioning device 100, 300 according to various embodiments. In an embodiment the guidance system 200 may be an image based guidance system. The image based guidance system may include a radiation based system including a fluoroscope, X-ray machine, or C-ARM 226. As shown in FIGS. 1B and 1C, an electronic positioning device 100 may be coupled to a guidance system 200 boom 224. As also shown in FIGS. 1B and 1C, an electronic positioning device 300 may be coupled to a guidance system 200 chassis 210. The guidance system 200 may also include a battery system 400 having one or more batteries that may supply power to the electronic positioning device 100 or 300.

Figure 2A:
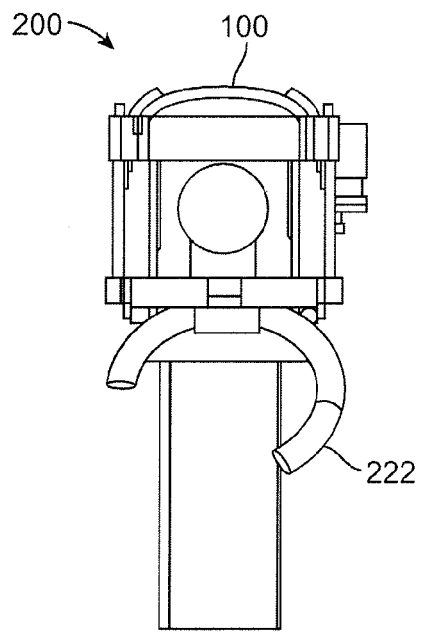
FIG. 2A is a back view of a boom electronic positioning device according to various embodiments.
Figure 2B:
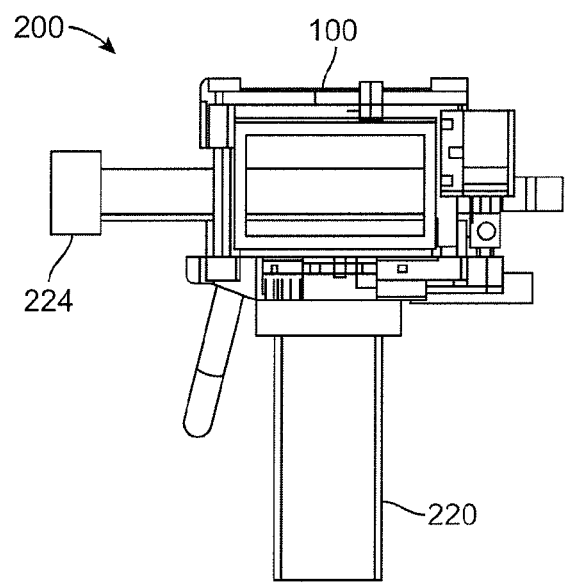
FIG. 2B is a side view of a boom electronic positioning device according to various embodiments.
Figure 2C:
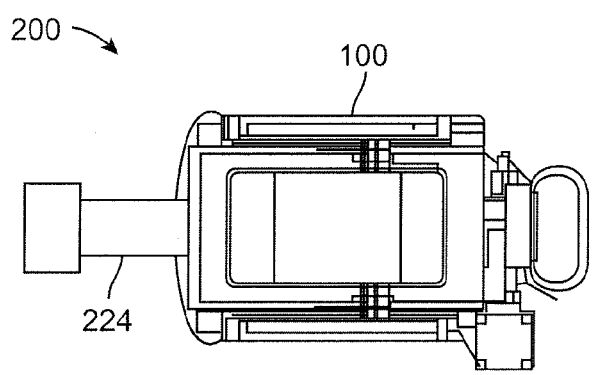
FIG. 2C is a top view of a boom electronic positioning device according to various embodiments.
Figure 2D:
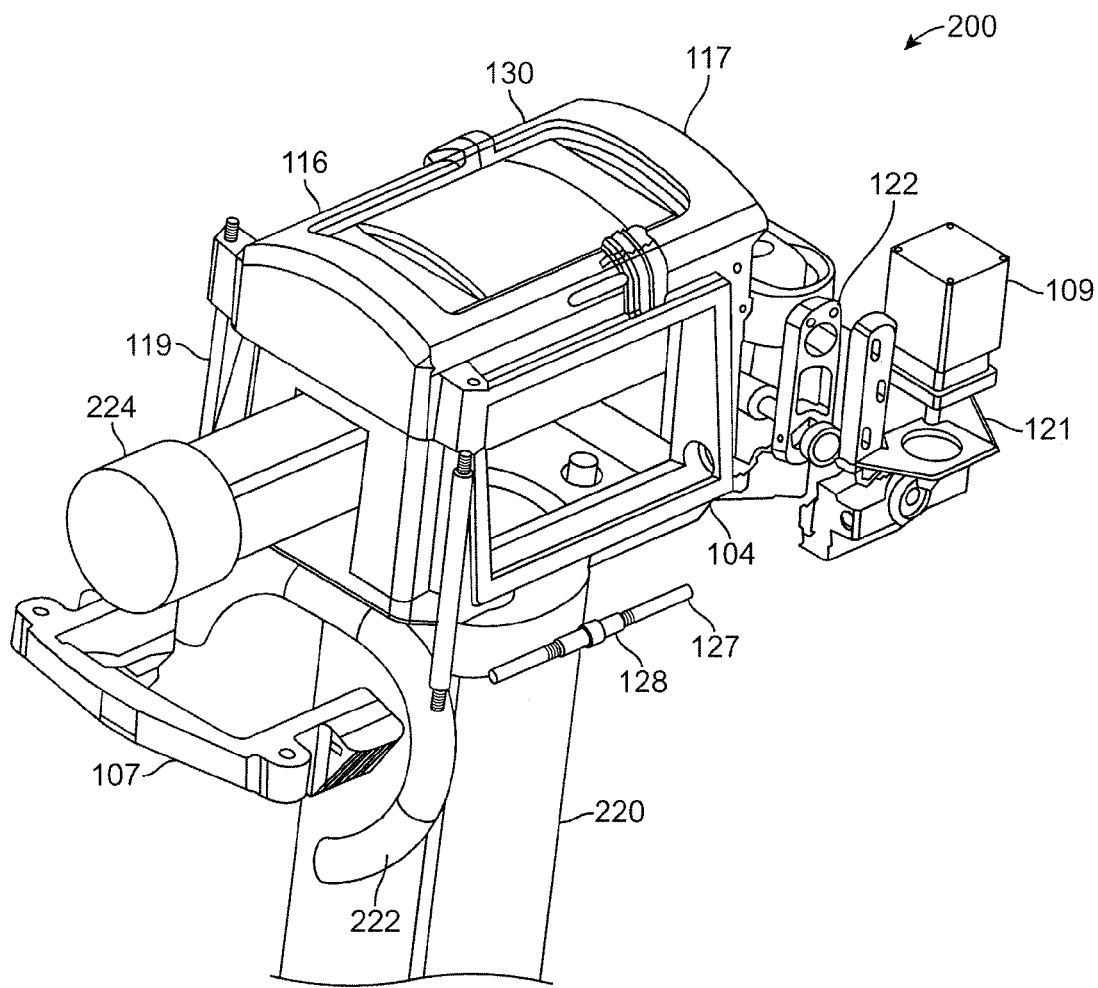
FIG. 2D is an isometric front side, partially exploded view of a boom electronic positioning device according to various embodiments.
Figure 2E:
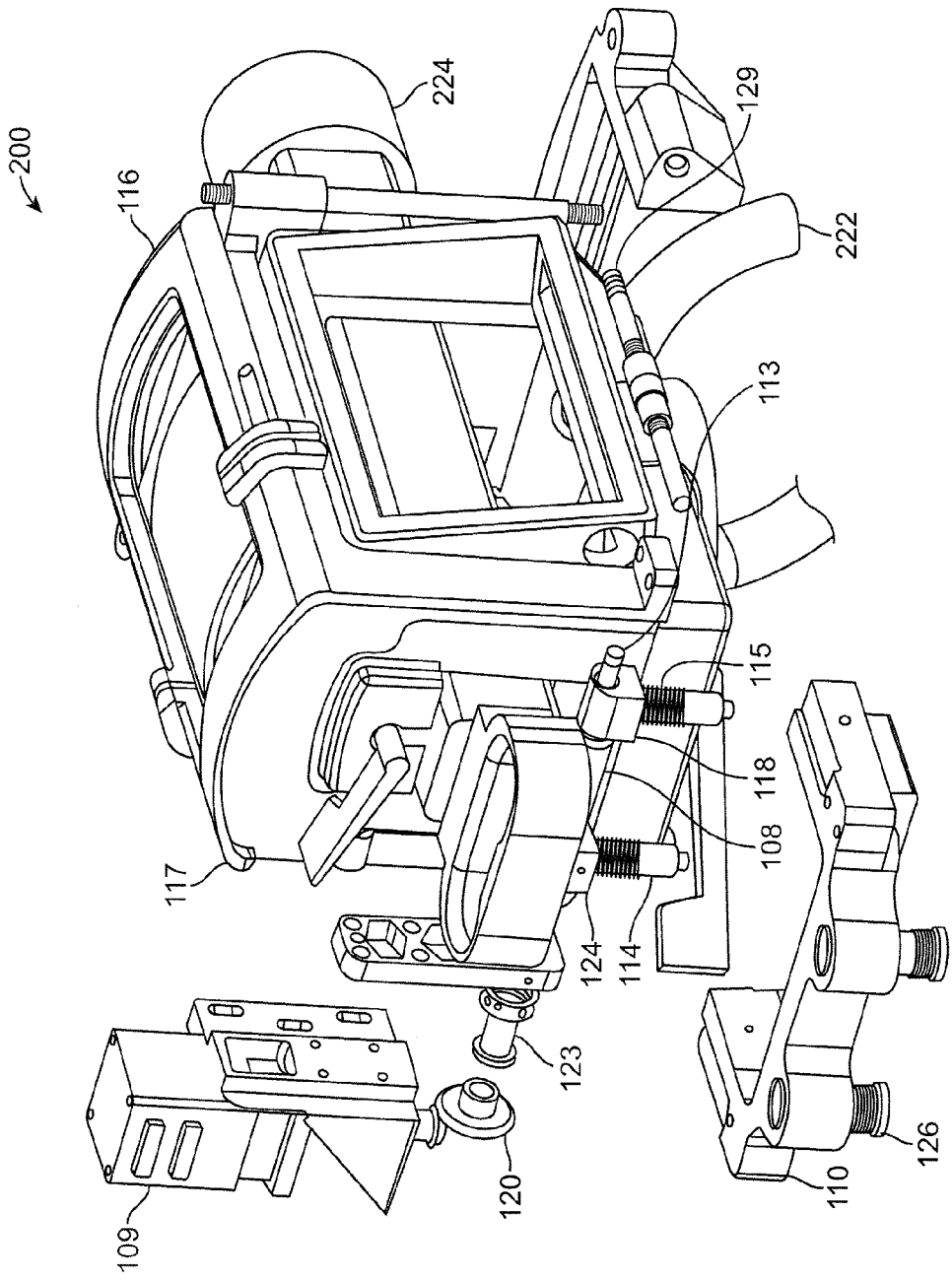
FIG. 2E is an isometric back side, partially exploded view of a boom electronic positioning device according to various embodiments.
Figure 3A:
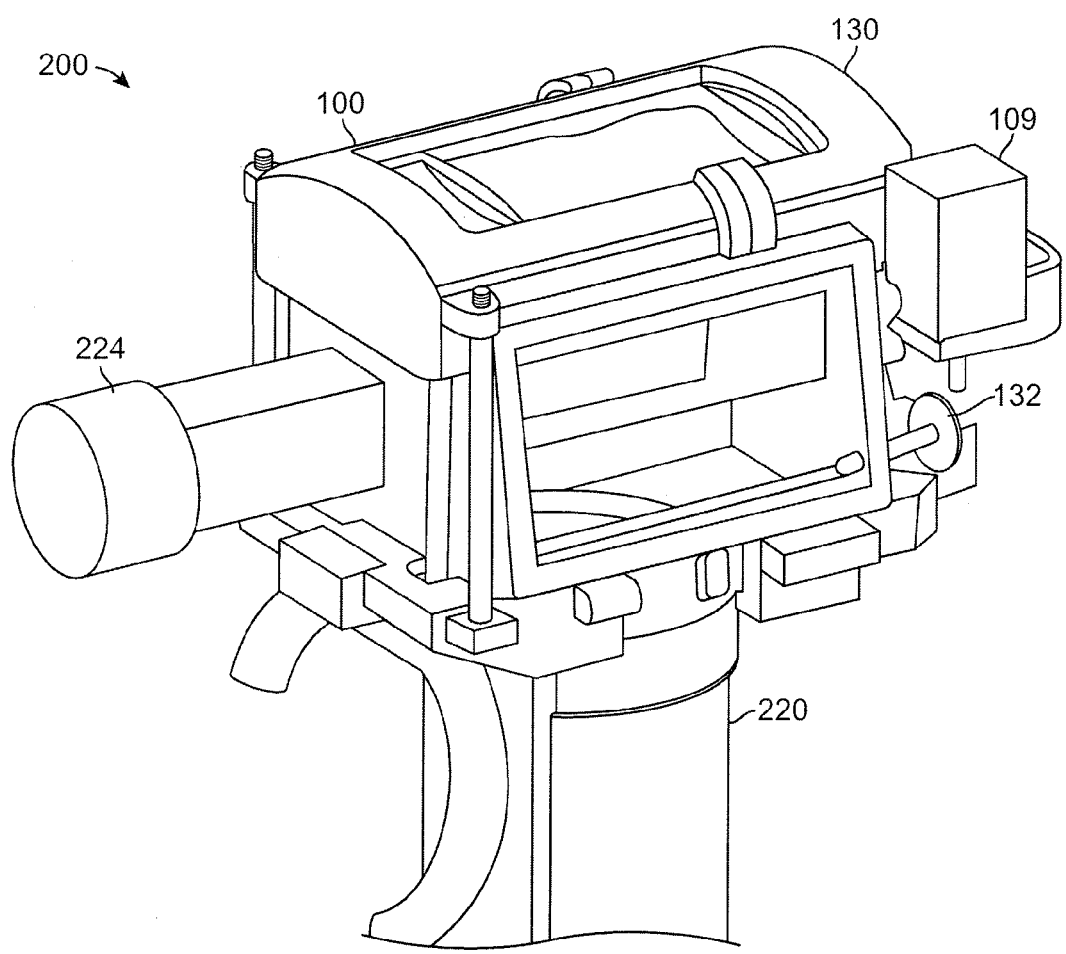
FIG. 3A is an isometric side view of a boom electronic positioning device according to various embodiments.
Figure 3B:
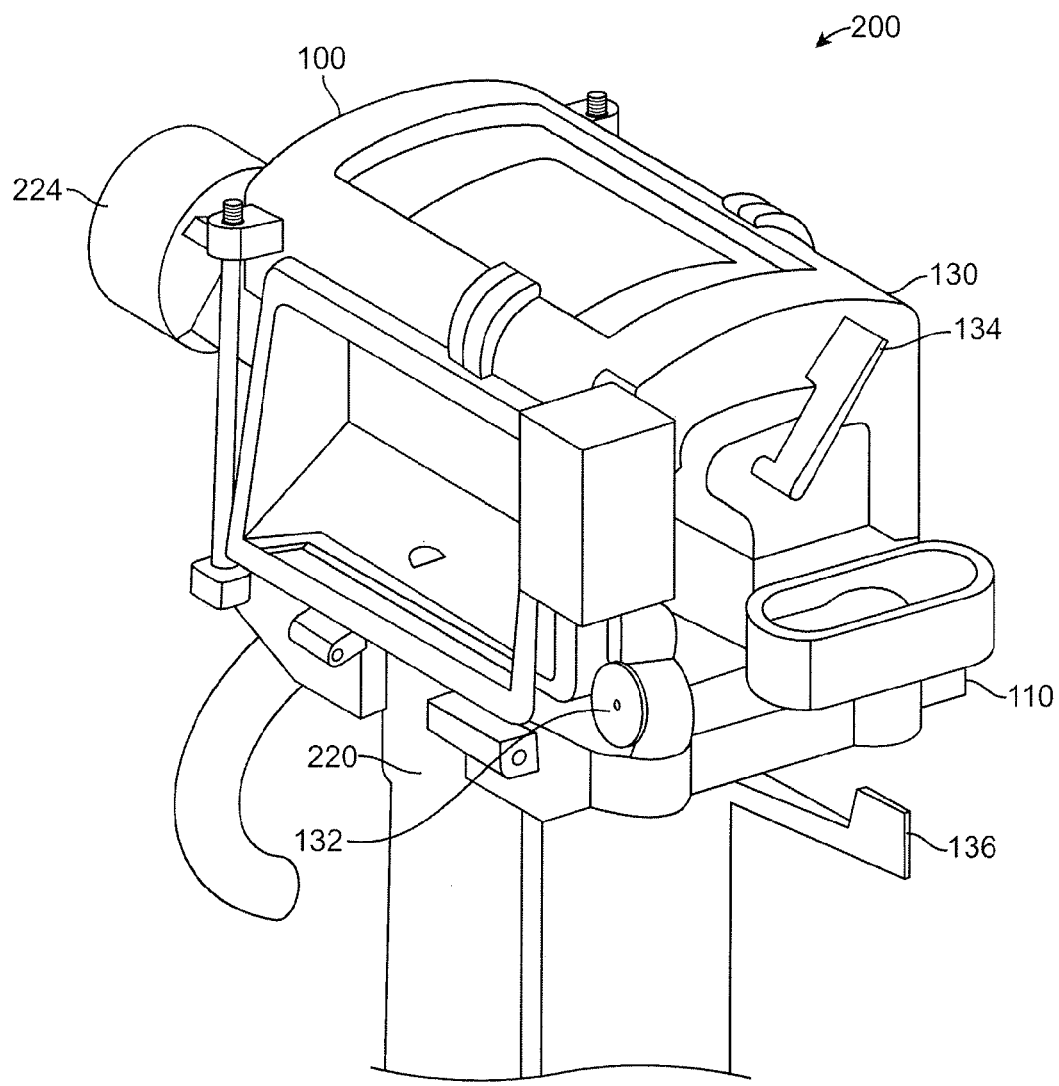
FIG. 3B is an isometric back view of a boom electronic positioning device according to various embodiments.
Figure 3C:
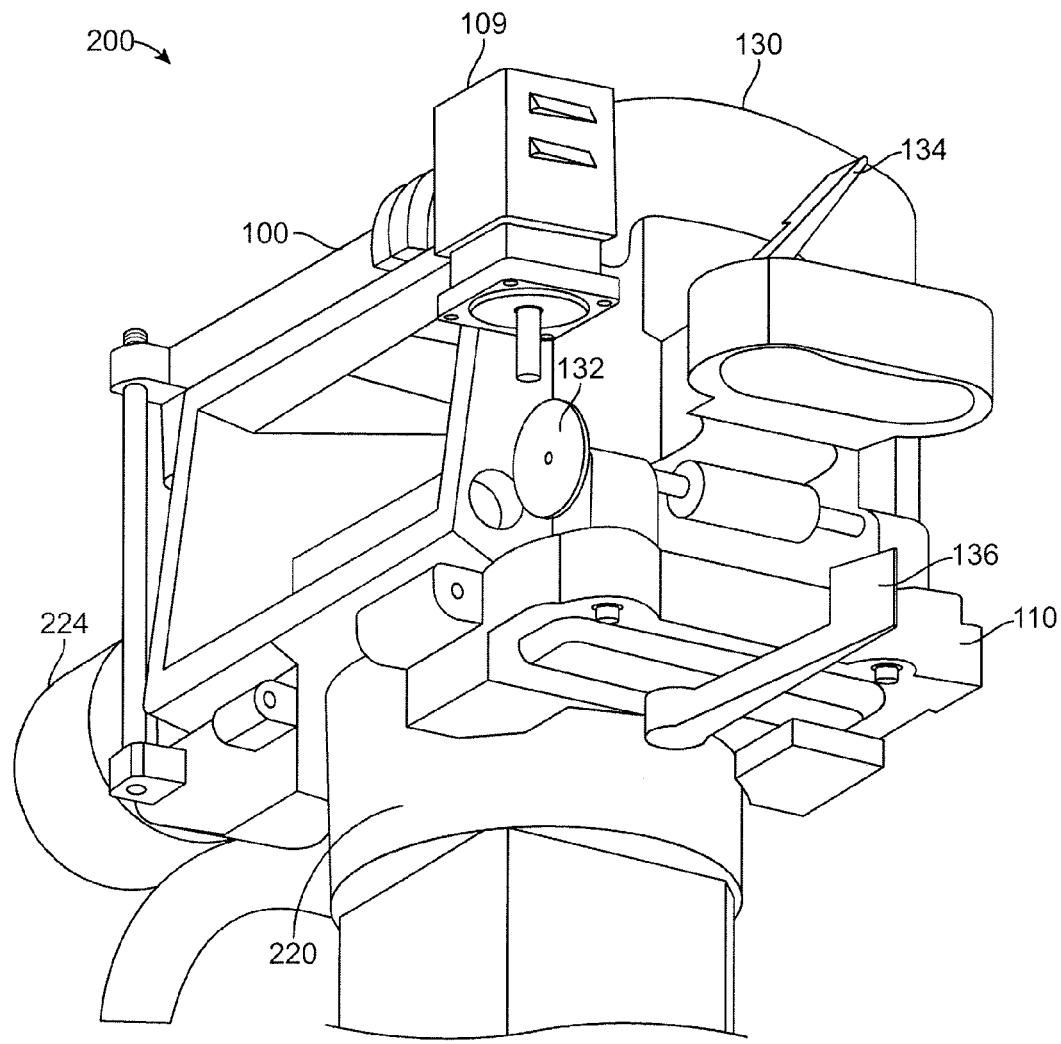
FIG. 3C is an isometric lower back view of a boom electronic positioning device according to various embodiments.
Figure 3D:
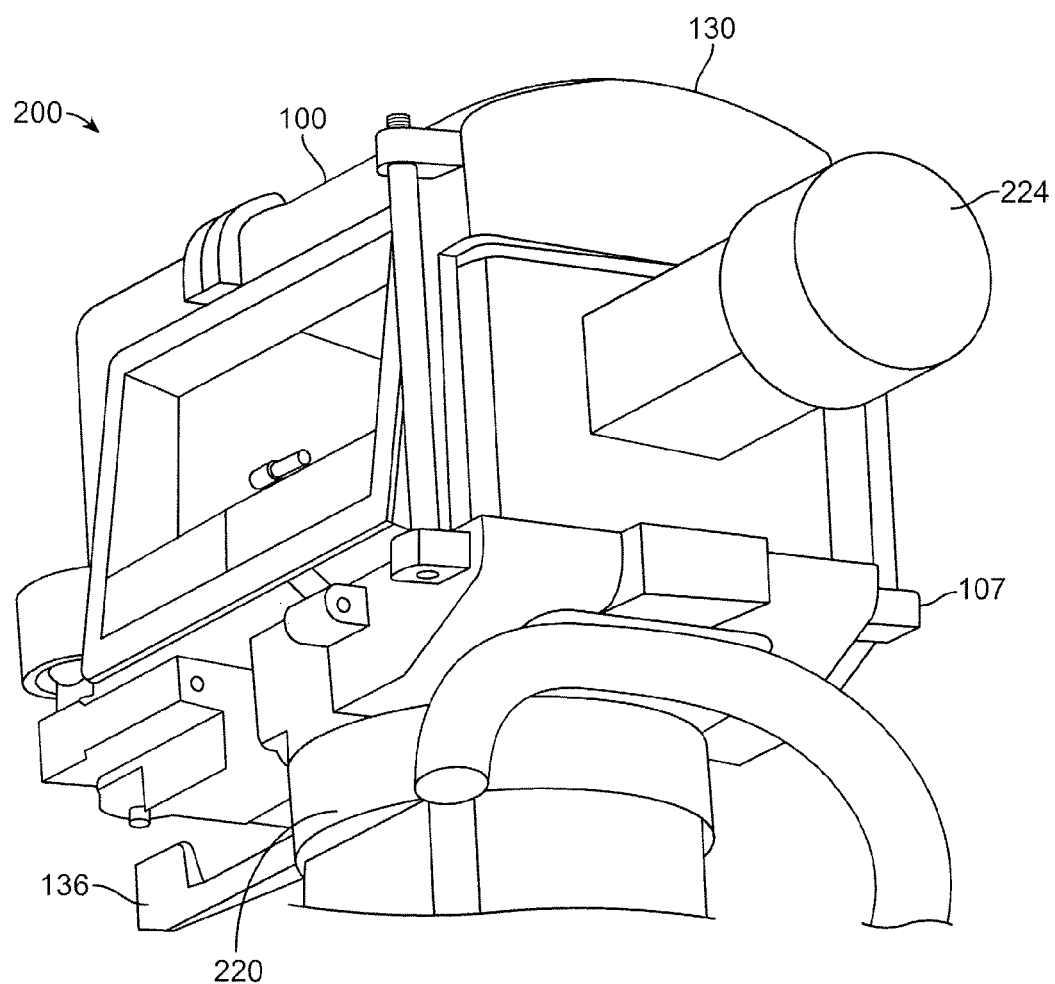
FIG. 3D is an isometric lower front view of a boom electronic positioning device according to various embodiments.
Figure 3E:
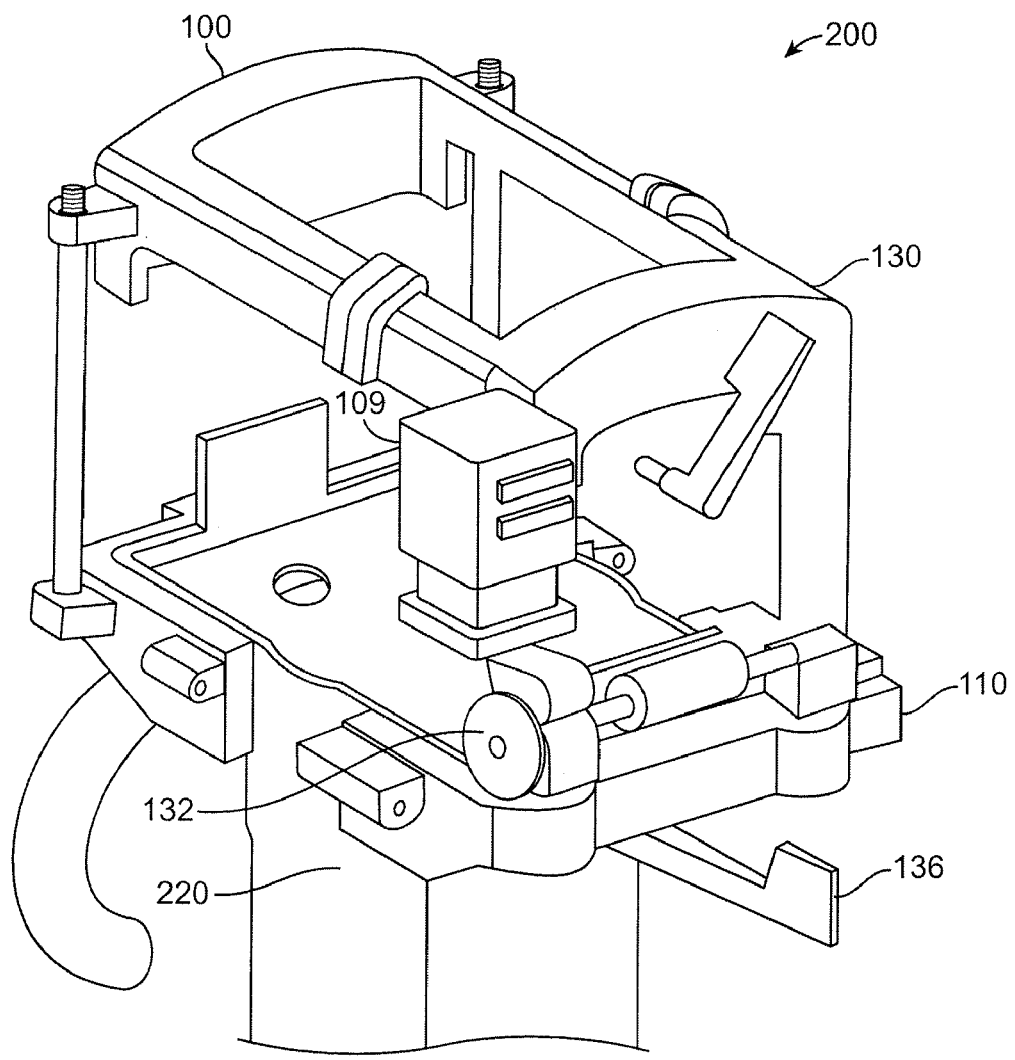
FIG. 3E is a partial isometric back view of a boom electronic positioning device according to various embodiments.
Figure 3F:
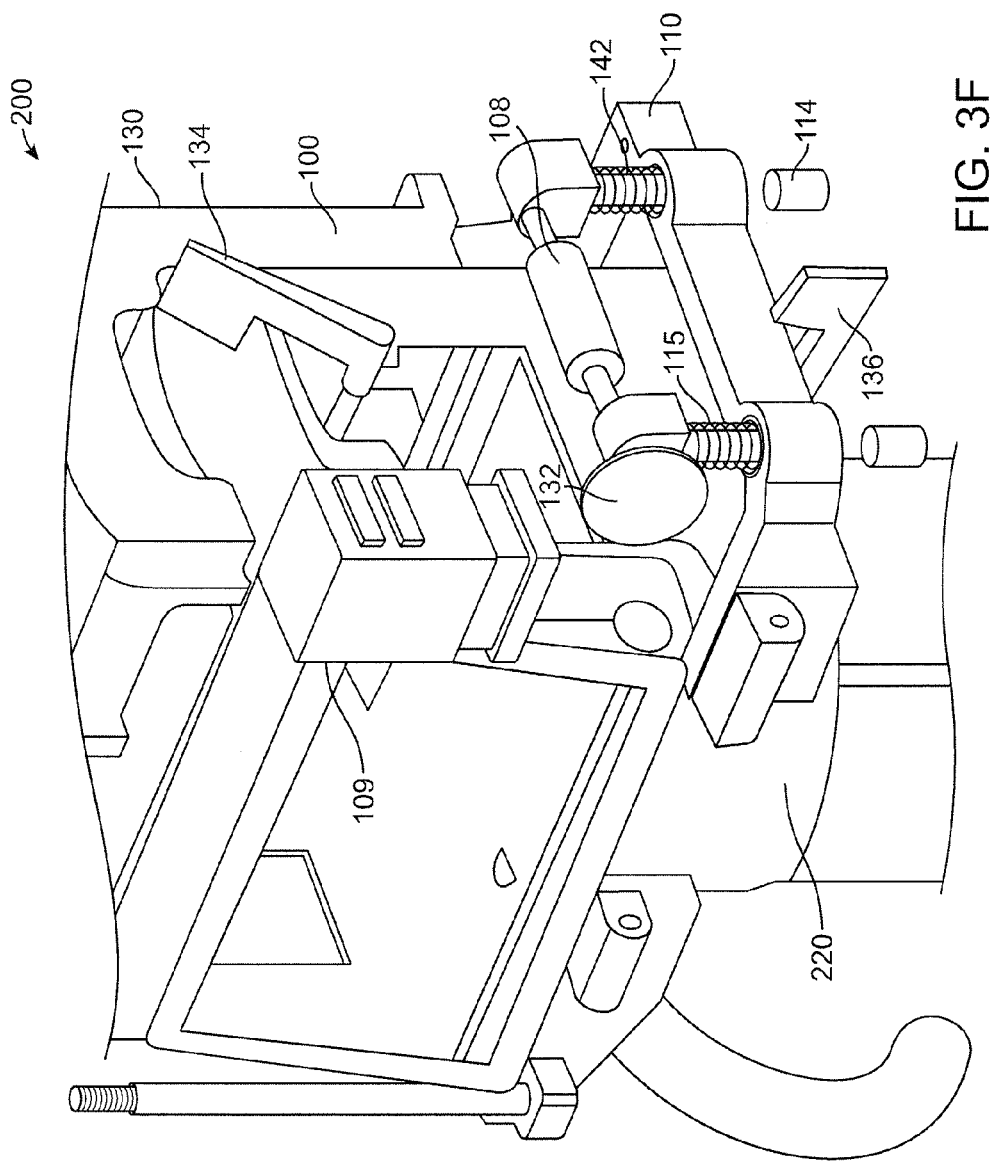
FIG. 3F is a partial exploded back view of a boom electronic positioning device according to various embodiments.
Figure 3G:
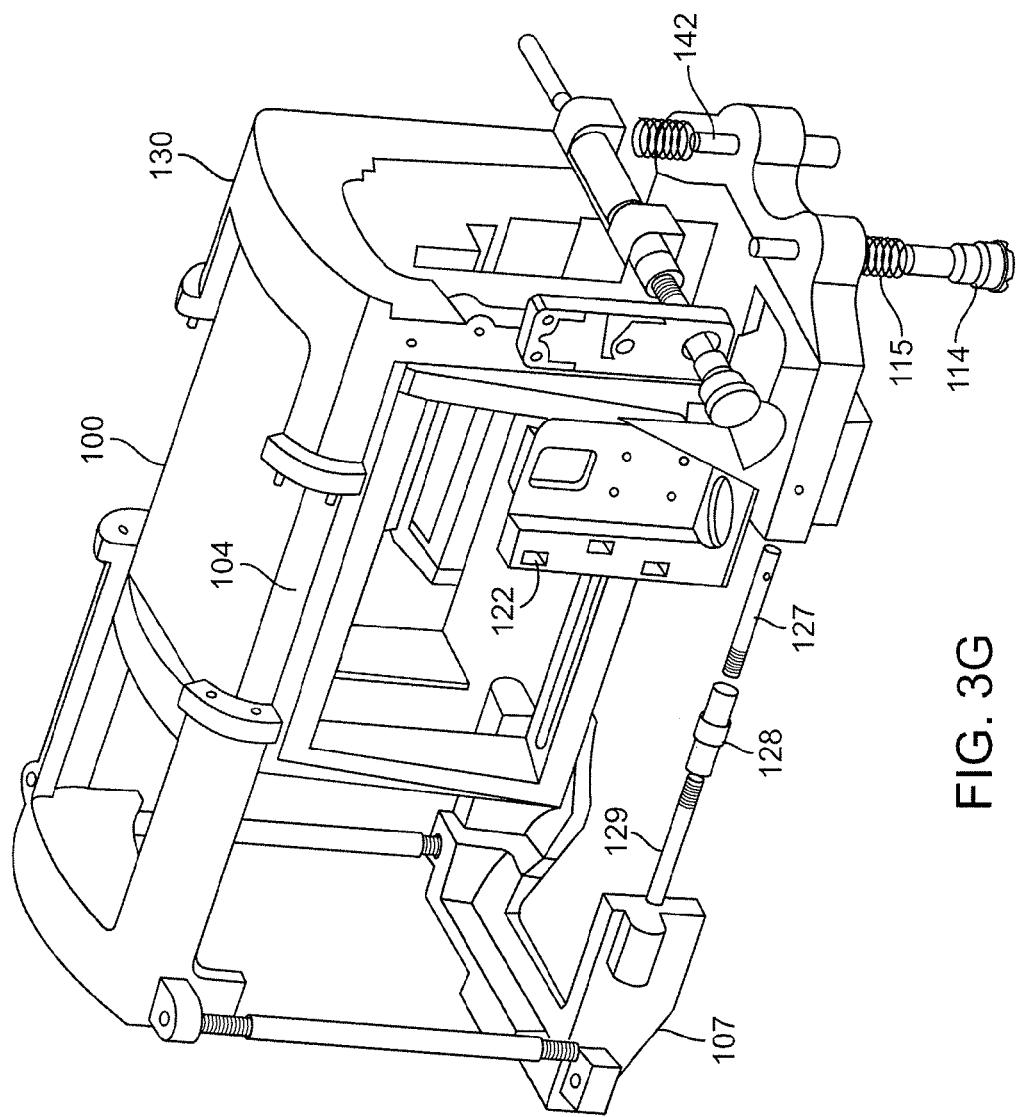
FIG. 3G is an exploded side view of a boom electronic positioning device according to various embodiments.
Figure 3H:
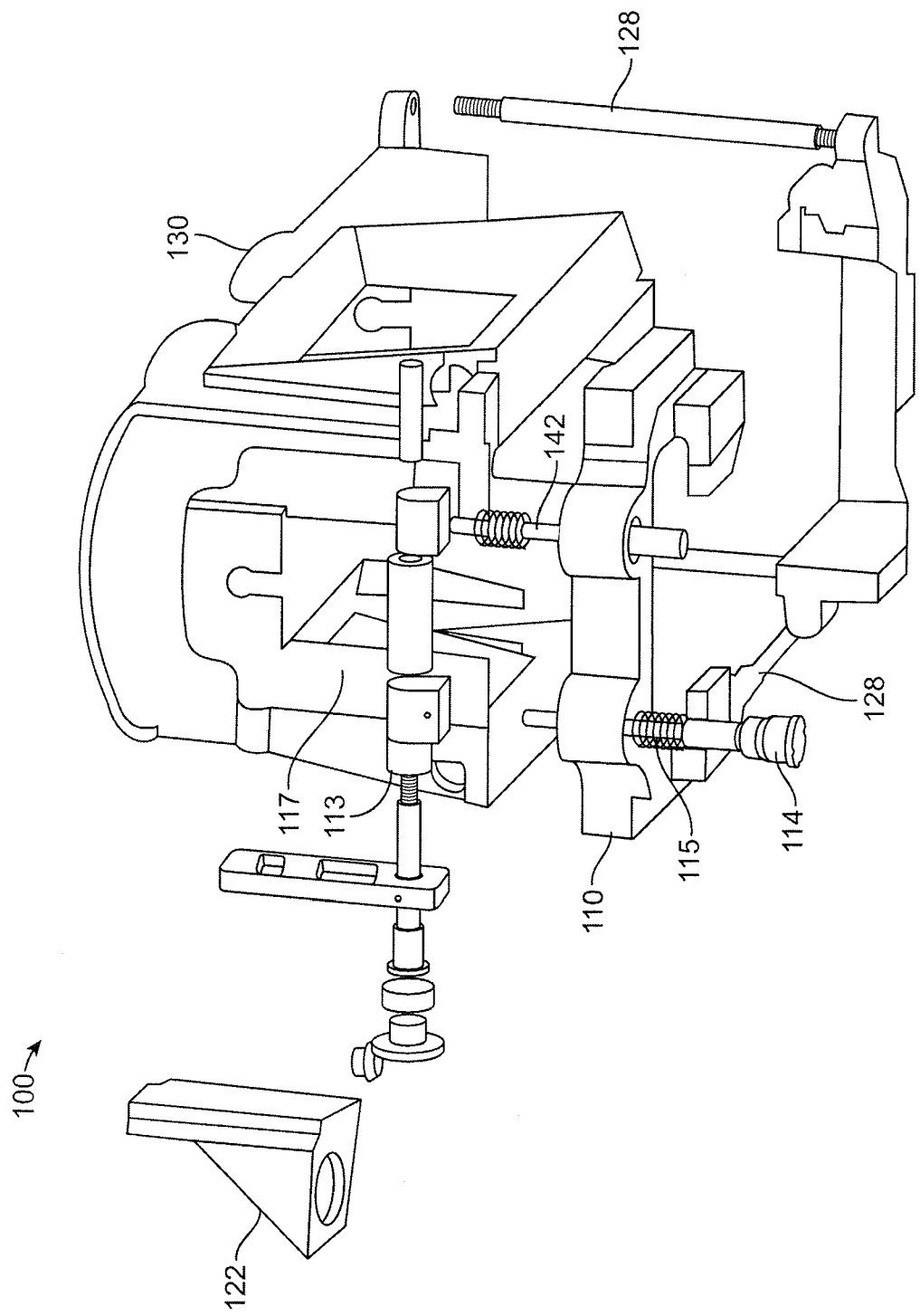
FIG. 3H is an exploded rear view of a boom electronic positioning device according to various embodiments.
Figure 3I:
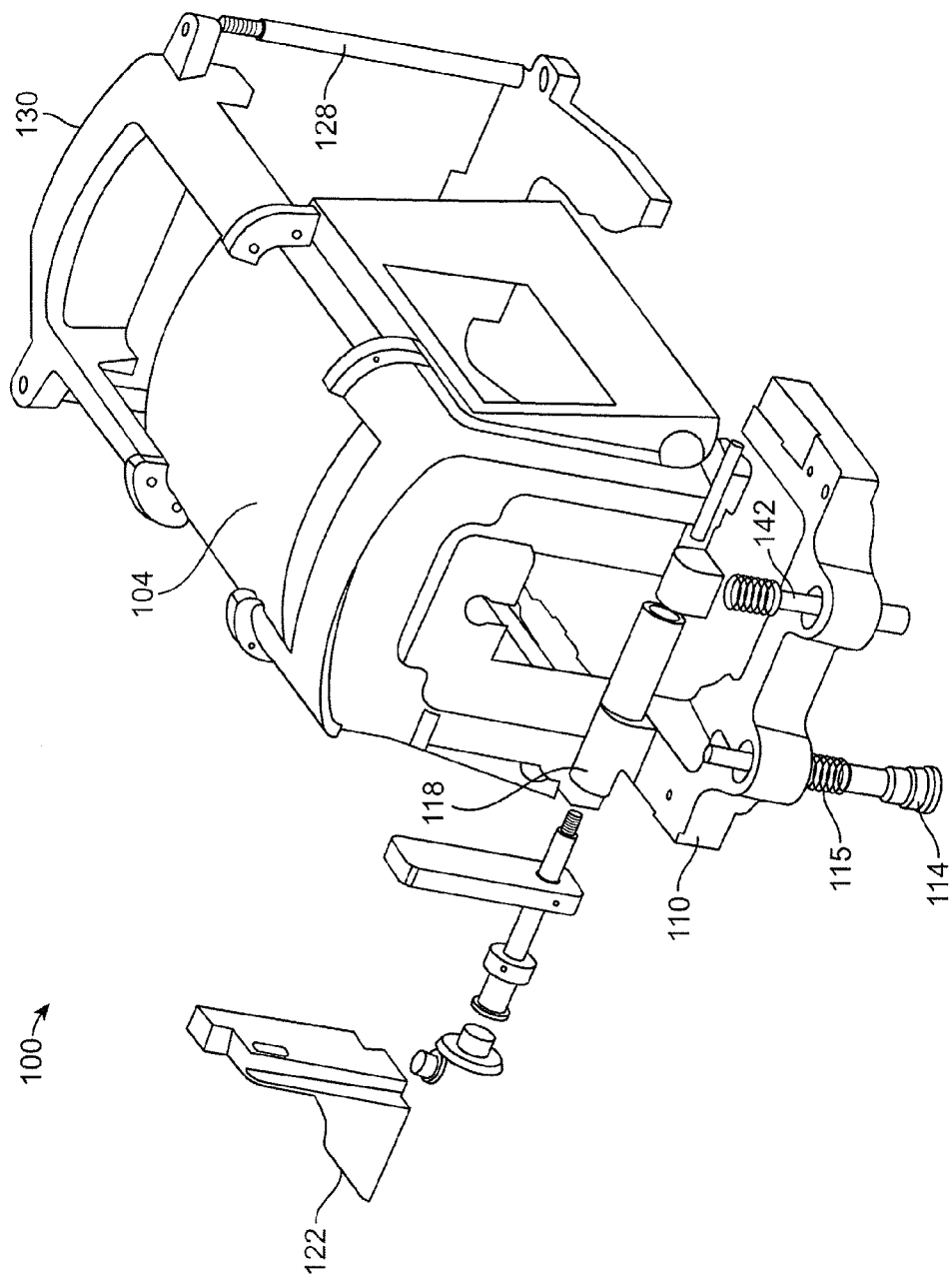
FIG. 3I is an exploded rear, top view of a boom electronic positioning device according to various embodiments.

In an embodiment the electronic positioning device 300 may be rotatably coupled to the guidance system 200 chassis 210. The electronic positioning device 100 may be rotatably coupled to the guidance system 200 via a boom 224 base or pedestal 220. FIGS. 2A to 3I are diagrams of the electronic positioning device 100 couplable to a guidance system 200 boom 224. FIG. 2A is a back view, FIG. 2B is a side view, FIG. 2C is a top view, FIG. 2D is an isometric front side, partially exploded view, FIG. 2E is an isometric back side, partially exploded view, FIG. 3A is an isometric side view, FIG. 3B is an isometric back view, FIG. 3C is an isometric lower back view, FIG. 3D is an isometric lower front view, FIG. 3E is a partial isometric back view, FIG. 3F is a partial exploded back view, FIG. 3G is an exploded side view, FIG. 3H is an exploded rear view, and FIG. 3I is an exploded rear, top view of a boom electronic positioning device according to various embodiments.

As shown in these figures the boom couplable electronic positioning device 100 may include a main housing 130 that couples a motor 109 driven boom roller to the boom 224. The positioning device 100 may include an internal housing 104, boom clamp 107, motor mount 121, standoff clamp 119, upper front clamp 116, superior distal boom clamp 117, arm bearing support 122, turnbuckle 128 having a right shaft 127 and left shaft 129, posterior arm roller 113, roller arm 118, linear ball bearings 114, journal fittings 124, Teflon® bearings 123, gear bevel 120, aft boom clamp 110, boom journal 126, spring 115, motor gear 132, boom locking arm 134, base locking arm 136, and shaft 142. In an embodiment the boom locking arm 134 may securely engage the boom 224. The base locking arm 136 may lock the boom base 220. The boom 224 may be adjustable along its axis and lockable via the boom lock lever 134. The boom 224 may rotatable on a pedestal/base 220 where the pedestal/base 220 may be lockable via a pedestal locking lever 136. The positioning system 100 may include an upper chassis 116 and a lower chassis 107 coupled together via one or more adjustable connecting rods 128.

A motor 109 may be coupled to the drive gear 132 where the motor 109 and drive gear 132 may be coupled to the chassis 104. The drive gear 132 may be coupled to a roller 108 that engages a section of the boom 224. The roller 108 may be coupled to the lower chassis 110 via extensions 142, springs 115, and bolts 114. In an embodiment the motor 109 may be a DC motor including a Parker™ IBE320 Servo DC motor. The gear 132 may be a 2 to 1 two bevel gear. The roller 108 may be a polyurethane roller. In an embodiment the motor 109, gear 132, and roller 108 are placed opposite the operation field of the guidance system 200.

In an embodiment the chassis 130, 107, 109 may include four clamping posts 128, 119. The lower chassis may comprise two segments 107, 109 coupled together via connectors 128 such as turn buckle draw bars. The upper chassis 130 may be coupled to the lower chassis via connectors 119 such as standoffs. In an embodiment emergency stop controls may be placed on opposite sides of the chassis 130, 107, 109. In an embodiment the roller 108 may coupled to the gear 132 via a shaft 142 coupled to the extensions 118 and blocks 113. In an embodiment the blocks may include bronze and other linear bearings 114.

Figure 4B:
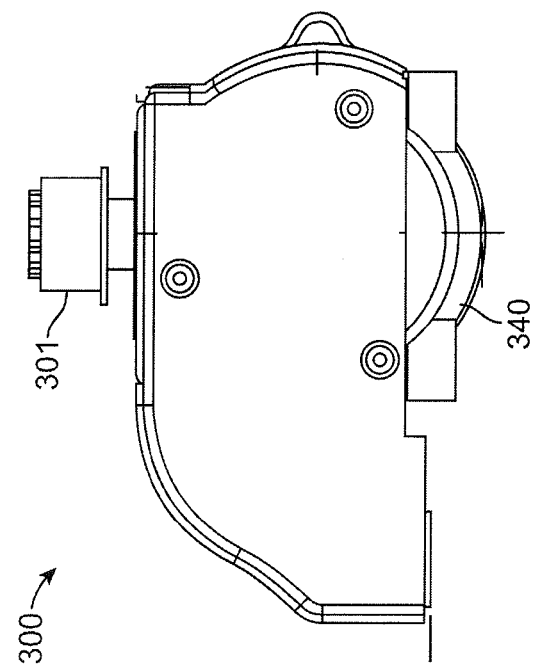
FIG. 4B is a side view of a chassis based electronic positioning device according to various embodiments.
Figure 4C:
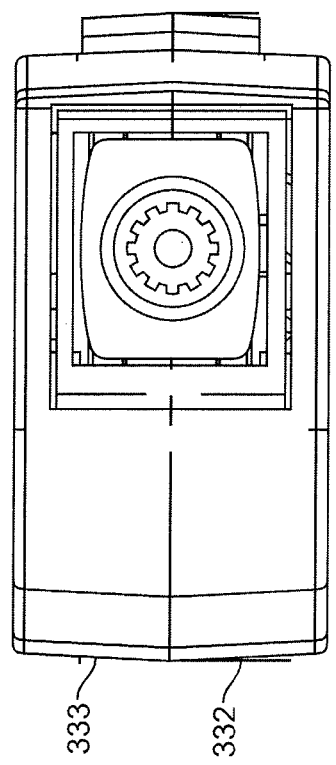
FIG. 4C is a top view of a chassis based electronic positioning device according to various embodiments.
Figure 4A:
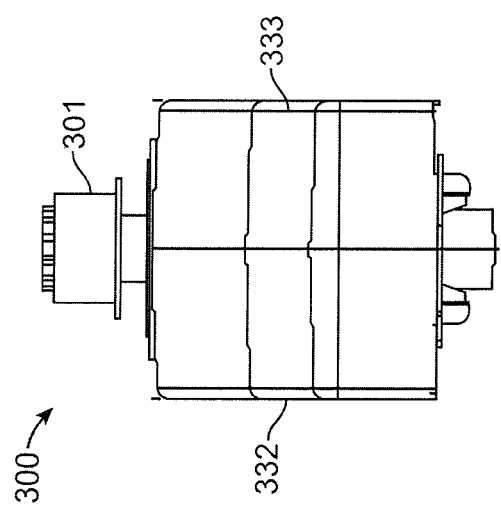
FIG. 4A is a back view of a chassis based electronic positioning device according to various embodiments.
Figure 4D:
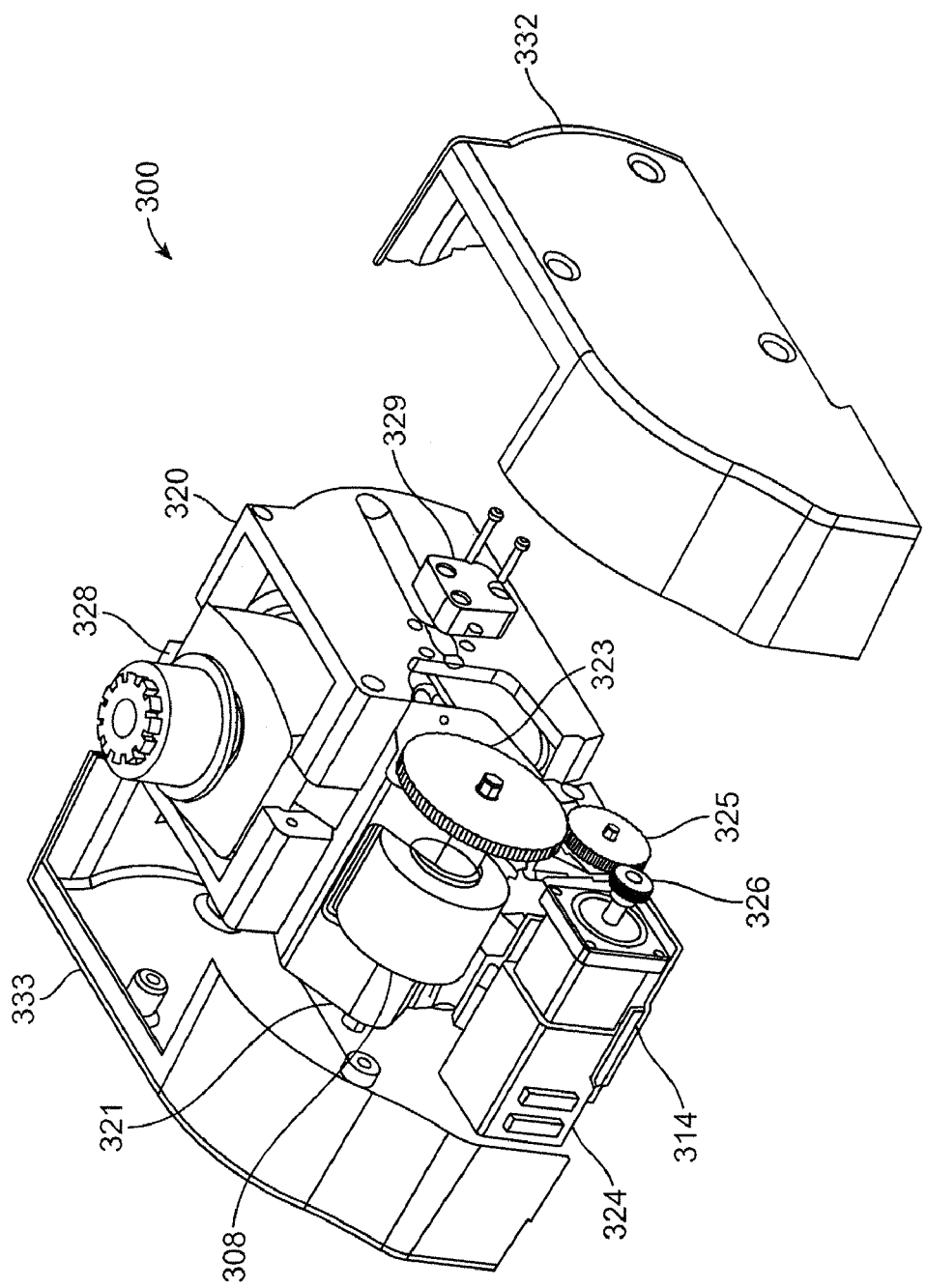
FIG. 4D is an exploded side view of a chassis based electronic positioning device according to various embodiments.
Figure 4E:
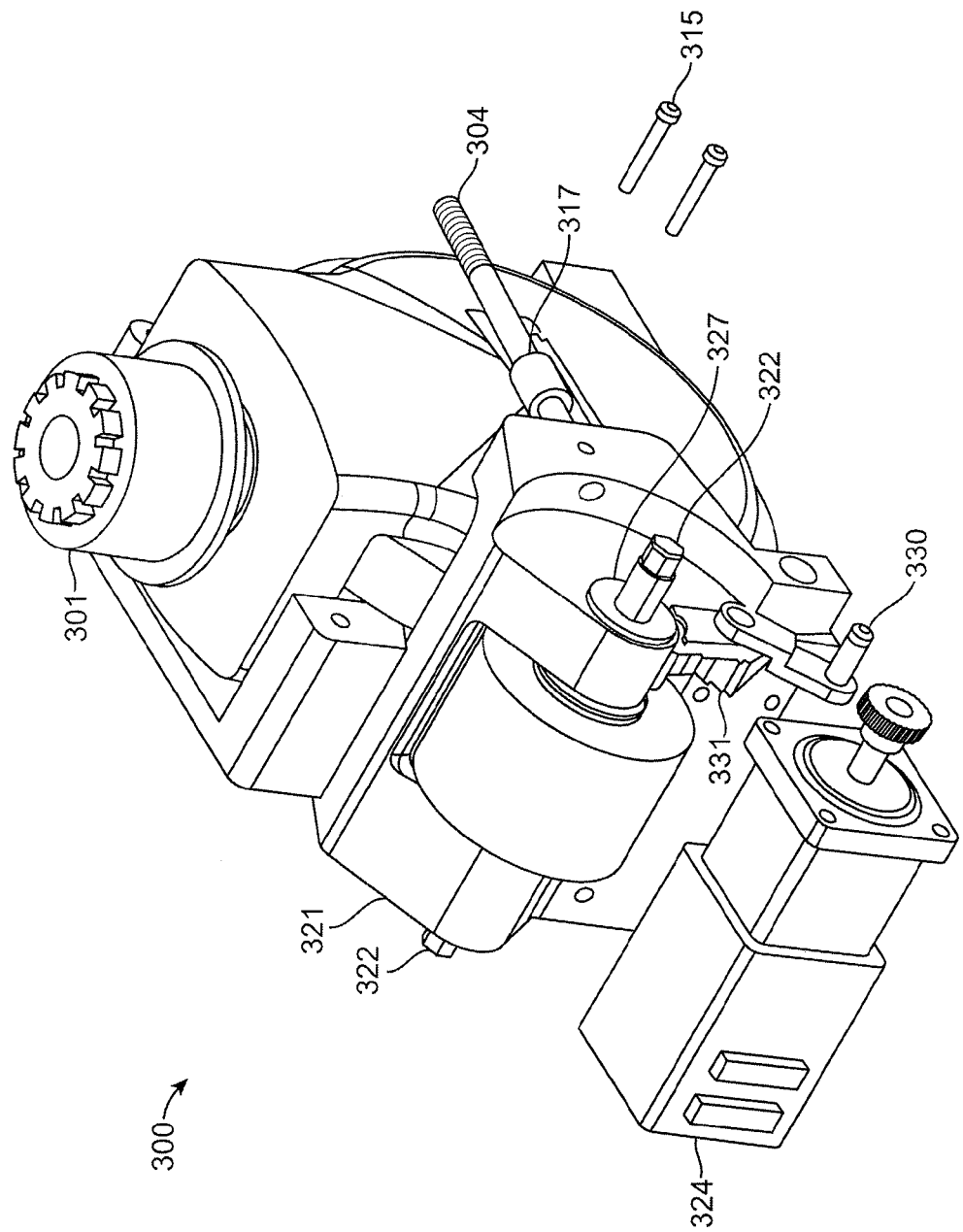
FIG. 4E is another exploded side view of a chassis based electronic positioning device according to various embodiments.

FIGS. 4A to 4E are diagrams of an electronic positioning device 300 that may coupled to a rotatable chassis wheel 340 of a guidance system 200 chassis 210. The wheel 340 may be coupled to the guidance system via a caster 301. In an embodiment the wheel 340 may be part of the device 300. FIG. 4A is a back view, FIG. 4B is a side view, FIG. 4C is a top view, FIG. 4D is an exploded side view, and FIG. 4E is another exploded side view of the chassis based electronic positioning device 300 according to various embodiments. The chassis based electronic positioning device 300 may include a left cover 333, right cover 332, caster wheel 301, wheel 340, left clam shell 320, right clam shell 328, block housing 329, drive 323, idler gear 325, driver gear 326, motor mount 314, DC motor 324, roller 308, gear head 321, roller shaft 322, cam follower 331, idler arm 330, flange 327, screws 315, linear ball bearings 317, and guide shaft 304.

In an embodiment the motor 324 may be a DC motor including a Parker™ IBE320 Servo DC motor. The drive gear 323 may be a 2 to 1 two bevel gear. The roller 308 may be a polyurethane roller. The electronic positioning device 100, 300 may be compatible with the commonly utilized image intensifier devices, including the GE/OEC model 9800 image intensifier. The devices 100, 300 may provide simple, controlled, and intuitive movement of the image intensifier along at least two axes. In an embodiment the axes may be orthogonal or perpendicular such as representing an X and a Y axis.

As shown in FIG. 1A the positioning devices 100, 300 may be coupled to a controller 230 having a plurality of buttons 232. The controller 230 may be coupled to a device 100, 300 via one or more wires 234 or via a wireless protocol. The controller 230 may enable a user to operate the devices 100, 300 from up to at least 10 meters from the system 200. The controller 230 buttons 232 may enable a user to translate or move the boom 224 or chassis 210 in micro and macro increments. In an embodiment the devices 100, 300 may move the boom 224 or chassis 1 mm upon each controller 230 activation. The boom 224 may have at least 3 cm of excursion in either direction along its axis (at least 6 cm total). The devices 100, 300 may also be operated by a foot switch 236 where the foot switch may override the controller 230 in an embodiment.

The foot switch 236 and controller 230 may be hermetically sealed or have sterilely accessible controls. When not active each device 100, 300 may disengage (the boom 224 or wheel 340) to allow unrestricted movement of the system 200. When active each device 100, 300 may engage (the boom 224 or wheel 340) to prevent movement of the system 200. Each device 100, 300 may allow varied rates of movement, e.g. as a device 100, 300 is activated for a predetermined time interval the movement rate may linearly increase.

While this invention has been described in terms of a best mode for achieving the objectives of the invention, it will be appreciated by those skilled in the art that variations may be accomplished in view of these teachings without deviating from the spirit or scope of the present invention.

What is claimed is:

1. An apparatus, including:
   a first housing releasably coupled to a first moveable component of a medical guidance system, the guidance system having a target, and wherein movement of the first moveable component affects the target position;
   a first stepable motor coupled to the first housing;
   a first driving component coupled to the first stepable motor and capable of engaging the first moveable component, the first driving component moving the first moveable component when the first stepable motor is stepped and the first driving component engages the first moveable component;
   a second housing releasably coupled to a second moveable component of the medical guidance system, wherein movement of the second moveable component affects the target position;
   a second stepable motor coupled to the second housing; and
   a second driving component coupled to the second stepable motor and capable of engaging the second moveable component, the second driving component moving the second moveable component when the second stepable motor is stepped and the second driving component engages the second moveable component.

2. The apparatus of claim 1, wherein the first moveable component is a boom coupled to the target.

3. The apparatus of claim 2, wherein the medical guidance system has a moveable chassis and the second moveable component is a vertically rotatable wheel.

4. The apparatus of claim 1, wherein the medical guidance system has a moveable chassis and the first moveable component is a vertically rotatable wheel.

5. The apparatus of claim 1, wherein the first moveable component has a first movement axis and the first moveable component moves about a first predetermined distance when the first stepable motor is stepped and the first driving component engages the first moveable component.

6. The apparatus of claim 5, wherein the first predetermined distance is about one millimeter.

7. The apparatus of claim 5, wherein the second moveable component has a second movement axis and the second moveable component moves about a second predetermined distance when the second stepable motor is stepped and the second driving component engages the second moveable component.

8. The apparatus of claim 7, wherein the first predetermined distance is about one millimeter and the second predetermined distance is about one millimeter.

9. The apparatus of claim 7, wherein the first moveable component and the second moveable component are configured so the first movement axis is approximately orthogonal to the second movement axis.

10. The apparatus of claim 1, wherein the first moveable component is a boom coupled to a C-Arm including the target.

11. The apparatus of claim 10, wherein the medical guidance system is a fluoroscope.

12. A system, including:
a medical guidance system having
a first moveable component, a target, and wherein movement of the first moveable component affects the target position;
a first housing releasably coupled to the first moveable component;
a first stepable motor coupled to the first housing;
a first driving component coupled to the first stepable motor and capable of engaging the first moveable component, the first driving component moving the first moveable component when the first stepable motor is stepped and the first driving component engages the first moveable component;
a second moveable component, wherein movement of the second moveable component affects the target position;
a second housing releasably coupled to the second moveable component;
a second stepable motor coupled to the second housing; and
a second driving component coupled to the second stepable motor and capable of engaging the second moveable component, the second driving component moving the second moveable component when the second stepable motor is stepped and the second driving component engages the second moveable component.

13. The system of claim 12, wherein the first moveable component is a boom coupled to the target.

14. The system of claim 12, wherein the medical guidance system has a moveable chassis and the first moveable component is a vertically rotatable wheel.

15. The system of claim 12, wherein the first moveable component has a first movement axis and the first moveable component moves about a first predetermined distance when the first stepable motor is stepped and the first driving component engages the first moveable component.

16. The system of claim 15, wherein the first predetermined distance is about one millimeter.

17. The system of claim 15, wherein the second moveable component has a second movement axis and the second moveable component moves about a second predetermined distance when the second stepable motor is stepped and the second driving component engages the second moveable component.

18. The system of claim 17, wherein the first predetermined distance is about one millimeter and the second predetermined distance is about one millimeter.

19. The system of claim 17, wherein the first moveable component and the second moveable component are configured so the first movement axis is approximately orthogonal to the second movement axis.

20. The system of claim 12, wherein the medical guidance system is a fluoroscope.

21. The system of claim 12, wherein the first moveable component is a boom coupled to a C-Arm including the target.

22. The system of claim 21, wherein the medical guidance system is a fluoroscope.

* * * * *